United States Patent [19]

Abraham

[11] Patent Number: 5,688,262
[45] Date of Patent: Nov. 18, 1997

[54] LASER MICROSCOPE ADAPTOR APPARATUS WITH AUTO-FOCUS

[75] Inventor: Martin David Abraham, Hod Hasharon, Israel

[73] Assignee: Laser Industries Ltd., Tel Aviv, Israel

[21] Appl. No.: 368,994

[22] Filed: Jan. 5, 1995

[30] Foreign Application Priority Data

Jan. 14, 1994 [IL] Israel ......................................... 108335

[51] Int. Cl.[6] .................................................. A61N 5/06
[52] U.S. Cl. ............................. 606/18; 606/17; 606/13; 606/2
[58] Field of Search ........................................ 606/2, 3–17

[56] References Cited

U.S. PATENT DOCUMENTS

| | | |
|---|---|---|
| 3,783,874 | 1/1974 | Koester et al. .................. 606/4 |
| 3,982,541 | 9/1976 | L'Esperance, Jr. .............. 606/18 |
| 4,000,417 | 12/1976 | Adkisson et al. . |
| 4,694,151 | 9/1987 | Yoshimma . |
| 4,719,912 | 1/1988 | Weinberg ...................... 606/4 |
| 5,128,509 | 7/1992 | Black et al. . |
| 5,216,235 | 6/1993 | Lin . |
| 5,364,390 | 11/1994 | Taboda et al. ................. 606/3 |

*Primary Examiner*—David M. Shay
*Attorney, Agent, or Firm*—Corbin Gittes & Samuel

[57] ABSTRACT

A laser micromanipulator for surgical applications includes an adaptor attachable to a laser and to a microscope which automatically maintains, preferably using phase detection, the laser beam in focus on tissue during any changes in the working distance by the surgeon manipulating the microscope.

1 Claim, 8 Drawing Sheets

LASER MICROSCOPE ADAPTOR APPARATUS WITH AUTO-FOCUS

FIELD AND BACKGROUND OF THE INVENTION

The present invention relates to a laser microscope adaptor apparatus with auto-focus. The invention is particularly useful in surgical laser microscope apparatus for delivering a laser beam to an object, such as a tissue to be cut, removed, or coagulated and is therefore described below with respect to such application.

Surgical lasers are widely used in microsurgery, such as ENT, neurosurgery or gynecology, wherein a working laser beam (e.g., from a $CO_2$ laser), and a visible aiming beam (e.g., from a HeNe laser), are directed to the surgical site through a microscope adaptor, commonly termed a laser micromanipulator which includes a joystick by which the surgeon can direct the laser beam over selected locations in the field of view. Until recently, surgical microscopes were used at fixed working distances depending on the particular clinical application. For example, for vocal cord treatments, a working distance of 400 mm is normally used; whereas for neurosurgery, a working distance of 300 mm is normally used. Working distances are set by changing the objective lens on the microscope. To focus the laser beam at the focal plane of the microscope, laser focusing lenses in the micromanipulator are chosen in accordance with the working distance set on the microscope.

Recently, microscopes with variable working distances have been developed and applied clinically in various specialities. These microscopes, which may cover the range from 200 to 400 mm, enable the surgeon to electronically control and change the working distance from the microscope to the tissue during the surgical procedure. To maintain the laser beam in focus on the tissue under these circumstances, the surgeon is required to constantly change or move the lenses on the micromanipulator in accordance with the changes on the microscope.

One manufacturer has recently developed a micromanipulator in which the laser focusing lenses are electronically linked to the lenses on the microscope so that any change in the microscope is automatically also made in the laser micromanipulator. This method, however, requires elaborate electronic linkage between the microscope and the laser micromanipulator. Moreover, it does not allow versatility in using the same micromanipulator with operating microscopes of different manufacturers.

OBJECT AND BRIEF SUMMARY OF THE INVENTION

An object of the present invention is to provide an adaptor attachable to a laser and to a microscope which automatically maintains the laser beam in focus on tissue during any changes in the working distance by the surgeon manipulating the microscope.

According to the present invention, there is provided an adaptor attachable to laser apparatus and to a microscope for directing a laser beam from the laser apparatus onto an object in a working plane as viewed via the microscope, comprising: an optical system to be located in the path of the laser beam for focusing the laser beam onto the object in the working plane; a manipulatable mirror between the optical system and the working plane, which mirror is manipulatable to direct the laser beam to any desired location in the working plane; and an auto-focus system for receiving light from an object in the working plane and for automatically controlling the optical system in accordance therewith for focusing the laser beam onto the object in the working plane.

The auto-focus system may be any known system, such as widely used in cameras, for example. A preferred system is one based on the phase detection method as used in commercial single lens reflex auto-focus cameras.

It will be appreciated that the optical system which focuses the laser beam onto the object in the working plane may focus the laser beam to a very small diameter, e.g., for cutting tissue, or to a larger diameter, e.g., for ablating or coagulating tissue. In the latter case, the laser beam is sometimes referred to as being somewhat "defocused" to enlarge its diameter, and thereby to distribute the energy over a larger surface area. The adaptor of the present invention automatically focuses the laser beam onto the working surface, such that the beam as applied to the object will be precisely in the same form as outputted by the optical system, i.e., either a small-diameter "focused" beam or a larger-diameter somewhat "defocused" beam.

According to further features in the preferred embodiments of the invention described below, the laser apparatus outputs a working laser beam and a visible aiming laser beam. The manipulatable mirror is dichroic to reflect visible light from the object to the auto-focus system, and to transmit visible light including the visible laser aiming beam from the object to the microscope. The auto-focus system includes a visible light detector, a second dichroic mirror for reflecting the laser beams via a first optical path to the object in the working plane, and for transmitting the visible light from the object via a second optical path to the visible light detector; and a control system for controlling the optical system in response to the output of the visible light detector.

According to further features in the described preferred embodiment, the optical system includes a first optical device which focuses the laser beams to a focal plane between it and the second dichroic mirror, and a second optical device between the second dichroic mirror and the working plane and movable with respect to the first optical device to focus the laser beams exiting from the first optical device onto the working plane. The second dichroic mirror is located such that the optical path length from it to the focal plane is equal to the optical path length from it to the visible light detector. In addition, the first optical device is movable relative to the second dichroic mirror to increase or decrease the diameter of the laser beams applied to the object in the working plane.

Two embodiments of the invention are described below for purposes of example, in one embodiment, the first and second optical devices are both lens systems; and in a second described embodiment, they are mirror systems.

Since the adaptor constructed in accordance with the invention effects the focusing of the laser beam on the working plane via an auto-focus system incorporated into the optics of the micromanipulator, rather than in electronic linkage between the microscope and the micromanipulator, such an adaptor may be used for adapting laser apparatus to any type of microscope used in microsurgery and having the capability of varying the working distances. The invention thus eliminates the need for any electrical interface between the microscope and the laser micromanipulator. It is also useful with fixed distance microscope where critical laser focusing on tissue is desired.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
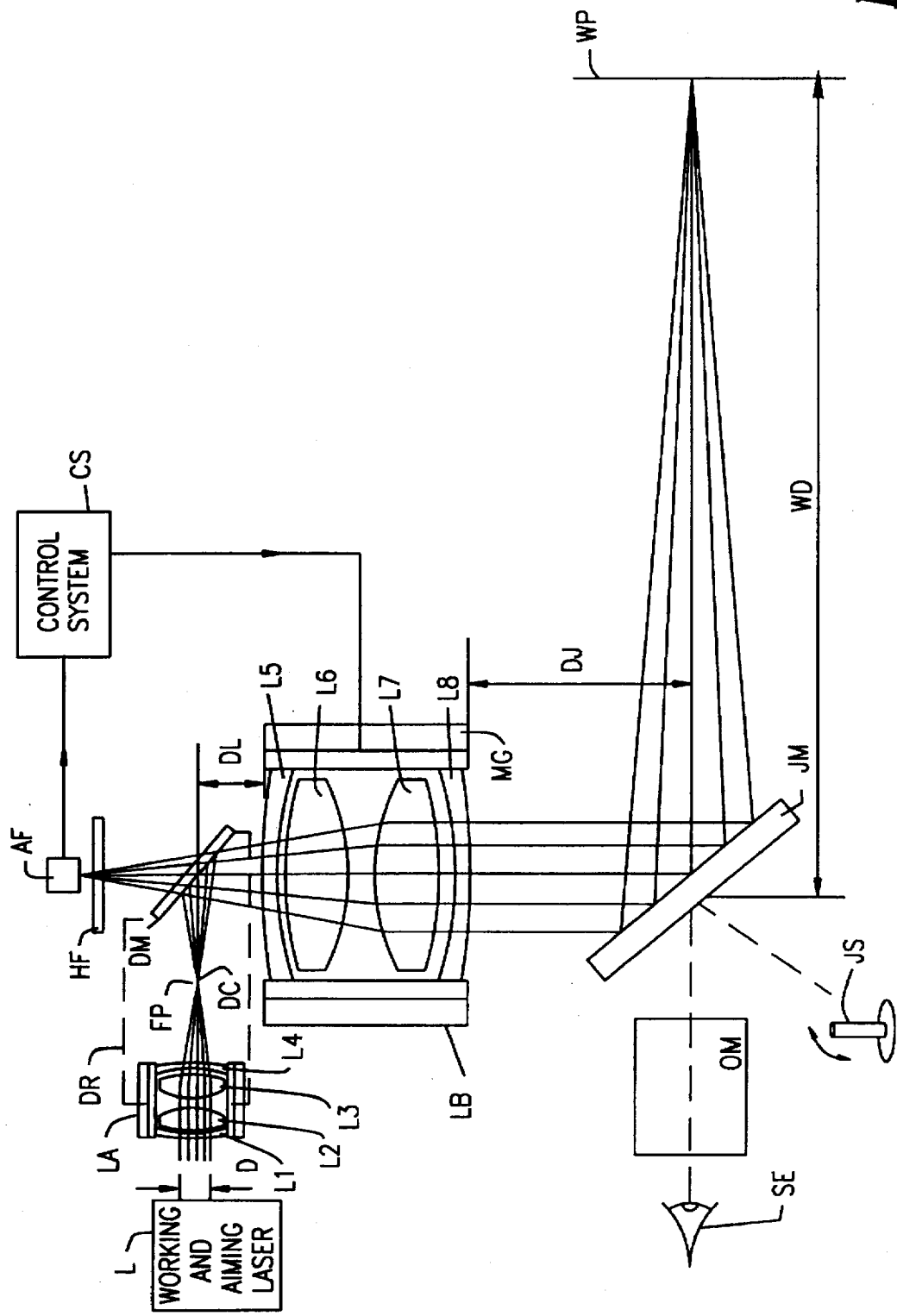
FIG. 1 illustrates one form of lens-based adaptor constructed in accordance with the present invention.

The Lens-Based Adaptor Illustrated in FIGS. 1–4

FIGS. 1–4 illustrate a lens-based micromanipulator adaptor comprising a Kepler type beam expander with two lens systems LA, LB, respectively. This adaptor is for use with laser apparatus L which outputs a working laser beam (e.g., from a $CO_2$ laser of 10.6 µ) and a visible aiming laser beam (e.g., from a HeNe of 0.633 µ). Each lens system LA, LB has both zinc selenide (ZnSe) elements and potassium bromide (KBr) elements for chromatic and spherical aberration correction, forming an aplanatic achromatic lens, as well known in the art. Each lens LA, LB is encapsulated with O-rings and a chemical moisture-absorbing material, evacuated, leak tested, and hermetically sealed.

The inputted laser beams, of a diameter "D", pass through the first lens system LA. This lens system contains four separate elements, namely two outer elements $L_1$, $L_4$ of ZnSe, and two inner elements $L_2$, $L_3$ of KBr. Lens system LA focuses the laser beams to the focal plane FP.

A 45° dichroic mirror DM is located on the other side of the focal plane FP. Dichroic mirror DM totally reflects the $CO_2$ laser beam and also the HeNe aiming beam to the second lens system LB. As will be described more fully below, dichroic mirror DM transmits the visible spectrum except for the HeNe aiming beam.

The laser beams, thus reflected by the dichroic mirror DM to lens system LB, are expanded. Lens system LB, of a similar type as lens system LA including two outer elements L5, L8 of ZnSe and two inner elements L6, L7, of KBr, focuses the laser beams via the joystick mirror JM onto the working plane WP. Joystick mirror JM is manipulatable by joystick JS to direct the beam to any desired location in the working plane WP. This mirror is also dichroic and is located at a 45° angle to the axis of lens system LB such that it reflects the two laser beams to the working plane WP, but passes visible light therethrough to enable the viewer SE to view the working plane via the operating microscope OM.

It will thus be seen that when the adaptor is installed on the operating microscope OM, the viewing optical axis is coincident with the laser beam axis, such that the surgeon's eye SE views the tissue as well as the laser aiming beam (HeNe) both of which pass through the dichroic mirror JM. The surgeon can thus precisely aim the working laser ($CO_2$) beam with respect to the tissue at the working plane as the surgeon views the working plane through the operating microscope.

Part of the visible light from the tissue at the working plane WP is also reflected by the joystick mirror JM back to the lens system LB. Dichroic mirror DM located between lens system LB and lens system LA transmits this visible light. A filter HF reflects only the aiming beam (HeNe) and transmits the remaining visible light to increase the signal-to-noise ratio. The transmitted light is focused by lens system LB onto an auto-focus detector AF of an auto-focus system, including a control system CS and a drive MG.

The auto-focus system operates in a manner similar to the operation of commercial auto-focus cameras. Thus, the auto-focus detector AF is connected via control system CS to the drive MG, such as a motor and gear system, for driving the lens system LB towards or away from the dichroic mirror DM, until the object in the working plane WP (namely the tissue viewed by the surgeon via the operating microscope OM) is focused on the auto-focus detector AF.

The focal length of lens system LB is the same at 10.6 µ (the wavelength of the $CO_2$ laser) as it is over the visible spectrum. For the $CO_2$ laser beam to be focused on the working plane WP as controlled by the auto-focus detector AF and its control system CS, the optical path length from the dichroic mirror DM to the auto-focus detector AF must be identical to the optical path length from the dichroic mirror to the focal plane FP of the lens system LA. This alignment is preferably carried out prior to use by the surgeon by changing the distance DC between the lens system LA and the dichroic mirror DM until the $CO_2$ laser beam is focused to a minimum spot diameter in the working plane WP. After this alignment has been preset, the focused minimum spot diameter will always coincide with the working plane WP irrespective of the working distance WD between the joystick mirror JM and the working plane WP.

Figure 2:
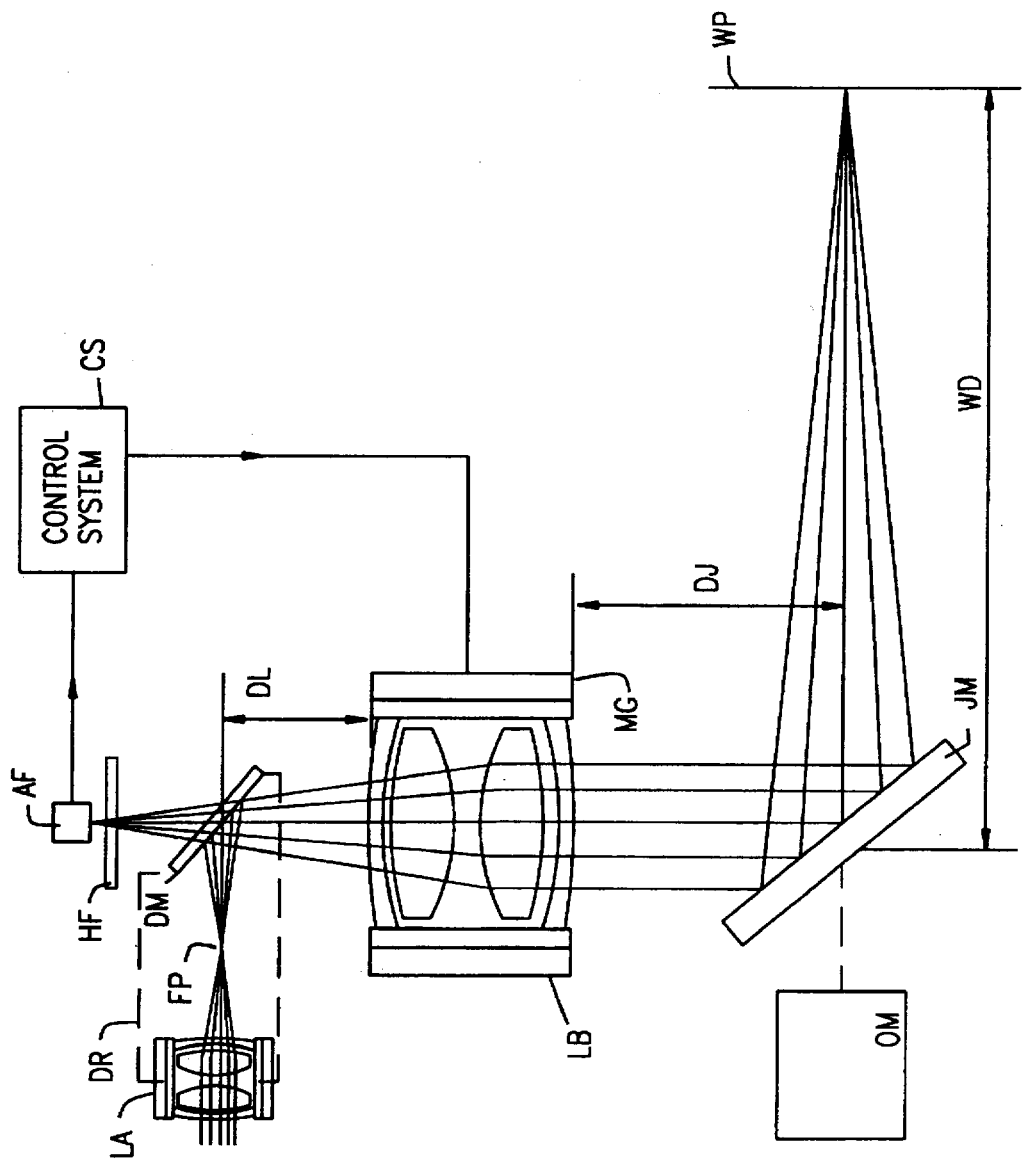
FIG. 2 illustrates how the laser beam in the adaptor of FIG. 1 are automatically focused on the object in the working plane when the working distance of the microscope is changed

The above will be better understood by reference to FIG. 2, illustrating what occurs when the surgeon has decided to shorten the working distance WD by one-half. The auto-focus system is activated, as described above by the auto-focus detector AF and its control system CS, to move the lens system LB away from the dichroic mirror DM. This increases the distance DL between the lens system LB and the dichroic mirror DM, and decreases the distance DJ between the lens system LB and the joystick dichroic mirror JM. The system thus automatically focuses the laser beams in response to changing the working distance WD of the operating microscope OM by the surgeon, thereby freeing the surgeon from making adjustments of the laser beam optical system.

Should the surgeon desire to work with an enlarged-diameter laser beam, e.g., for coagulation or ablation purposes, the surgeon can enlarge the diameter, or "defocus" the laser beam, by changing the distance DC from the lens LA to the dichroic mirror DM. This can be done with the aid of a defocus ring, shown schematically at DR in FIG. 1, as well known in the art. The preset amount of beam enlargement ("defocus") is maintained since the auto-focus detector AF receives information through the lens system LB alone. Thus, the operation of the auto-focus system including detector AF and its control system CS is completely independent of the sharpness of focus of the $CO_2$ laser.

Figure 3:
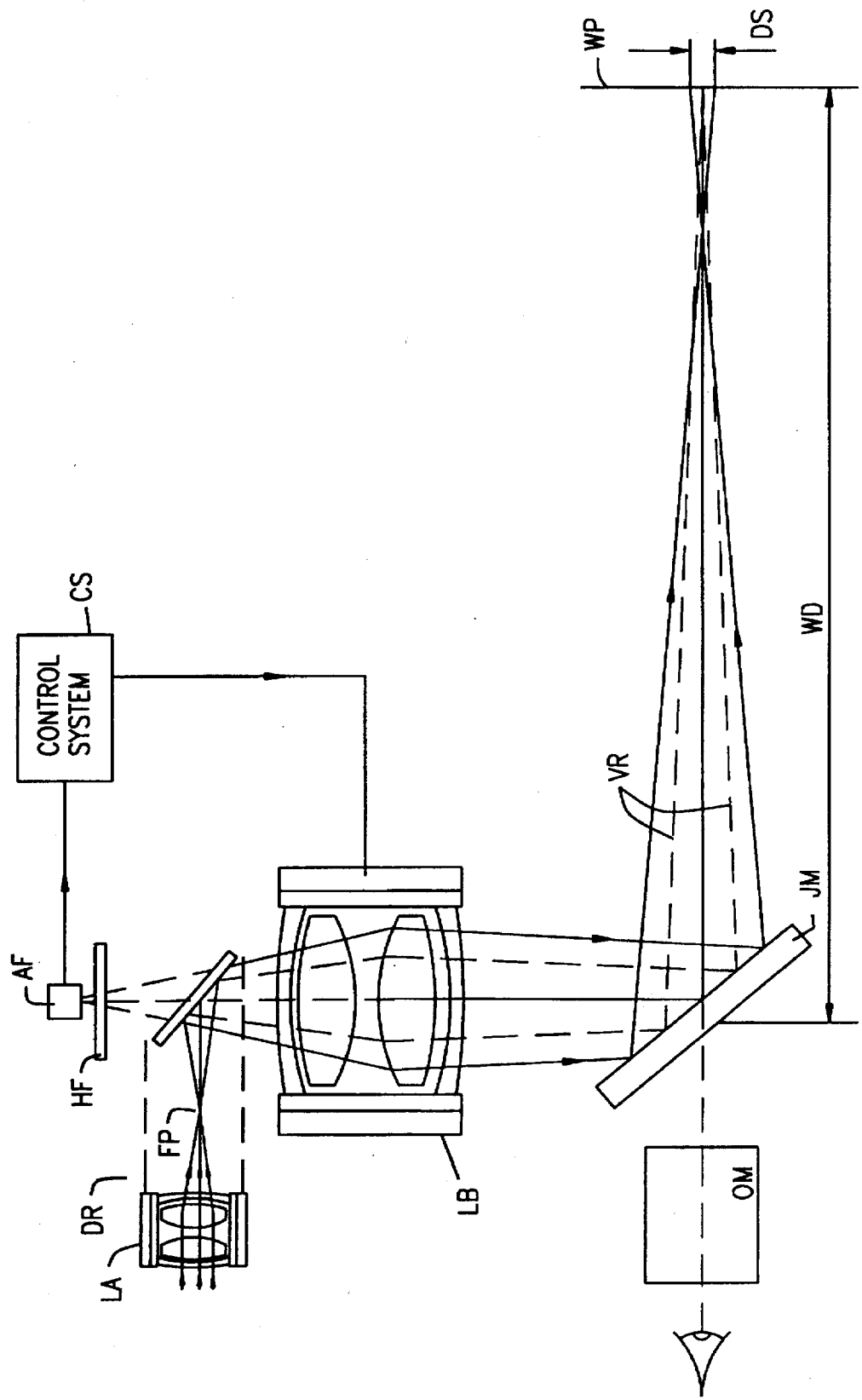
FIG. 3 illustrates the apparatus of FIG. 1 wherein the optical system is adjusted to enlarge the diameter or to "defocus", the laser beam.

The foregoing will be more apparent by reference to FIG. 3 which illustrates a defocus mode at a given working distance WD. In this situation, the surgeon would be operating with an enlarged ("defocused") spot diameter as shown at DS, where the working plane WP is the focal plane of the operating microscope. Rays of light in the visible part of the spectrum, as represented by the dashed lines VR, are propagated from the object (tissue), at the working plane WP through the system as described above, coming to a focus in the plane of the auto-focus detector AF. Thus, as far as the auto-focus detector is concerned, the object at the working plane WP is completely focused.

Figure 4:
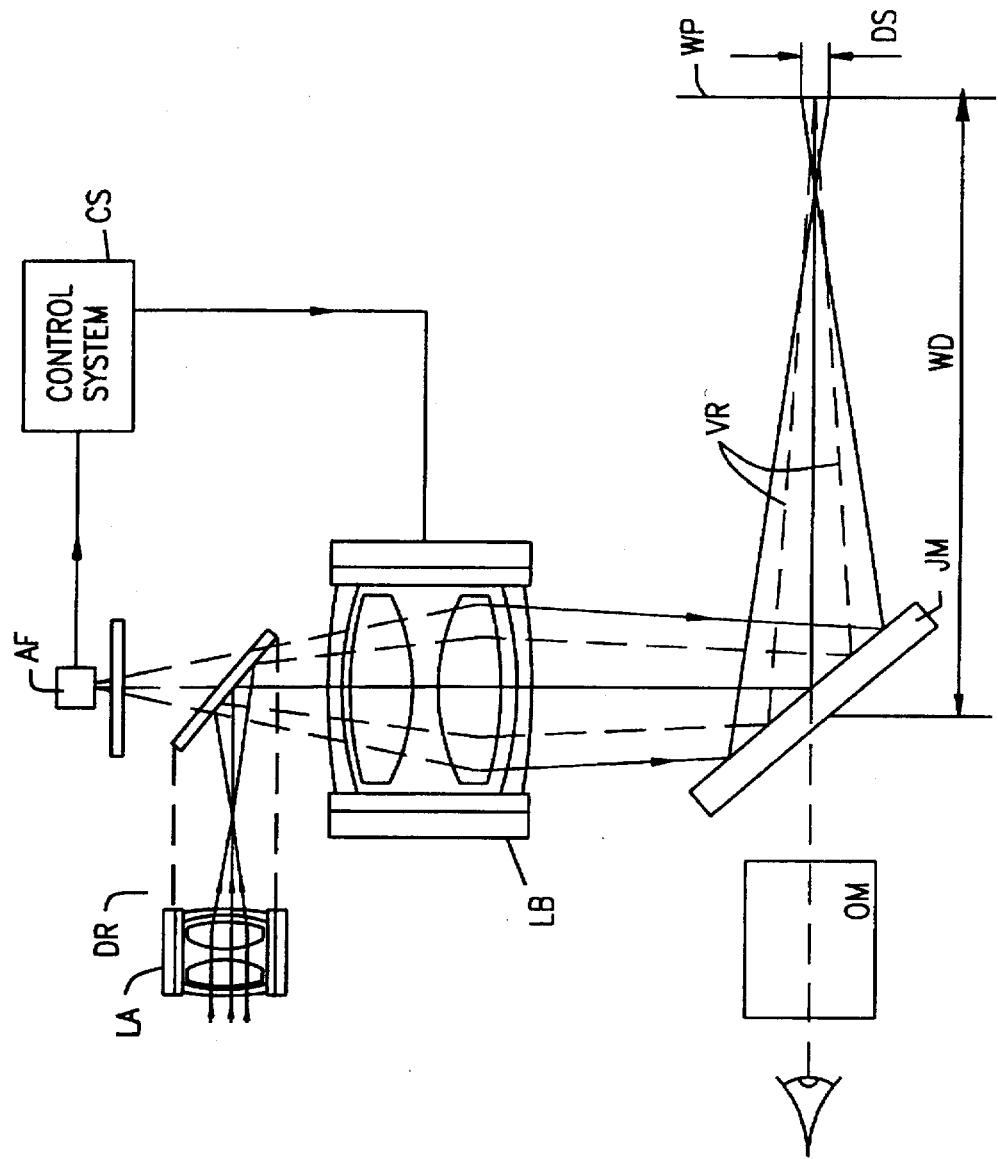
FIG. 4 illustrates how the "defocusing" effect is still maintained in the apparatus of FIG. 1 when the working distance is changed.

FIG. 4 illustrates the condition wherein the surgeon has operated the microscope OM to shorten the working distance by one-half. When the surgeon thus changes the working distance, the auto-focus system including detector AF and its control system CS automatically refocuses the lens system LB of the micromanipulator, thereby freeing the surgeon from this task. If the surgeon now wishes to work in the "focus" mode with a very small-diameter beam, the surgeon simply rotates the defocus ring DR to the position of "focus", as shown in FIG. 2.

The center of the HeNe aiming beam on the tissue at the working plane WP represents the center of the scene viewed by the auto-focus detector AF. The auto-focus mechanism may include a series of warning devices similar to the arrangement of commercial SLR cameras, These devices warn the surgeon that accurate focusing has not taken place for any one of a number of reasons. Thus, the ambient light level could be too low, or more likely there is not enough information in the viewed "scene" (i.e., the tissue in the working plane). The surgeon can change the scene by the auto-focus detector by moving the joystick JS which moves the aiming beam to a different viewed part of the tissue.

It will thus be seen that the surgeon can change the working distance WD by operating the microscope OM, or change the diameter of the operating laser beam by adjusting the defocusing ring DR, as and when required during an operating procedure, whereupon activation of the auto-focus system, including the auto-focus detector AF and its control system CS, will automatically maintain the laser beams focused at the selected beam diameter (i.e., precisely focused or preselectedly defocused) on the tissue in the working plane WP.

Mirror Based System

FIGS. 5-8 illustrate a mirror-based micromanipulator adaptor having an auto-focus operation of the laser beams which is basically the same as in the lens-based system of FIGS. 1-4.

Figure 5:
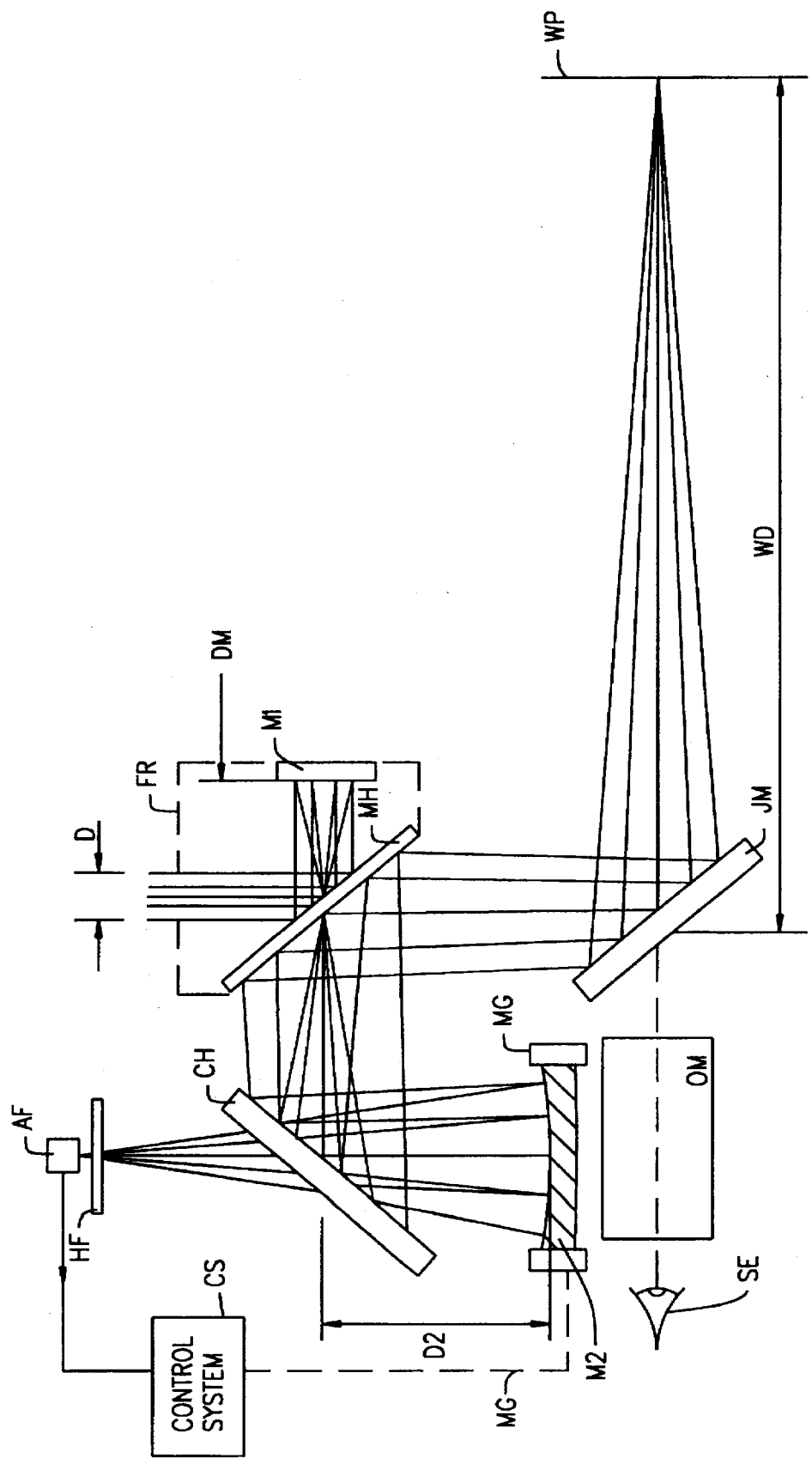
FIGS. 5, 6, 7 and 8 are diagrams corresponding to FIGS. 1, 2, 3 and 4, respectively, but with respect to a mirror-based adaptor system, rather than a lens-based adaptor as in FIGS. 1–4.

Thus as illustrated in FIG. 5, the input from the laser apparatus, containing both the working laser beam ($CO_2$) and the visible aiming laser beam (HeNe), both of diameter D, is reflected off a 45° planar reflector MH. Reflector MH is silvered on both surfaces and has a small conical hole drilled in its center. The reflected input beams strike focusing mirror M1, which has a concave non-spherical surface (Hyperbolic). The beams reflected from focusing mirror M1 come to a focus at a distance DH which is exactly where the hole in reflector MH is situated. The focussed beams pass through the conical hole in reflector MH and strike a dichroic combiner CH. This combiner totally reflects the $CO_2$ working beam and the HeNe aiming beam, while partially reflecting and partially transmitting the visible part of the spectrum. The reflected $CO_2$ and HeNe beams strike a concave spherical focusing mirror M2 at a distance D2 from the dichroic combiner CH.

The beams ($CO_2$ and HeNe) reflected off mirror M2 converge to a focus in the working plane WP. On the path to the focal plane they are reflected back by the dichroic combiner CH and reflector MH, and strike another dichroic mirror JM, which is the same joystick mirror described in the lens- based system of FIGS. 1-4. Mirror JM totally reflects the $CO_2$ beam while partially reflecting and partially transmitting the visible light (including the HeNe beam). The optical axis of mirror JM is coincident with the optical axis of the operating microscope OM whereby the working plane WP is at a distance WD from the joystick mirror. Focused working and aiming beams are thus formed in the working plane of the microscope.

The auto-focus optical channel is as follows: Visible rays emanating from the object (tissue) at the working plane WP are partly transmitted via the joystick mirror JM and the microscope OM to the viewer SE, constituting the viewing channel. These rays are partly reflected by the joystick mirror JM and by reflector MH and dichroic combiner CH to the focusing mirror M2. The rays are then reflected by mirror M2 and are transmitted through the dichroic combiner CH to the auto-focus detector AF. Filter HF is provided in the ray path as described in the lens-based system of FIGS. 1-4 to reflect only the visible aiming beam, and thereby to improve the signal to noise ratio. The AF control system activates the motor and gear system, schematically shown by the broken lines MG, coupled to the concave focusing mirror M2 to change the distance D2 until the object is completely focused on the auto-focus detector AF.

The working plane WP has now been focused as far as the AF detector is concerned. Since mirrors have exactly the same focal length irrespective of wavelength, the minimum $CO_2$ focused spot diameter will be formed on the working plane WP when the optical path length from the concave mirror M2 to the AF device, through the dichroic combiner CH and filter HF, is exactly the same as the optical path length from the concave mirror M2 to the focal plane of mirror M1, as described above with respect to the lens-based system of FIGS. 1-4. That is, in the system of FIGS. 5-8, the dichroic combiner CH is located such that the optical path from it to the hole in reflector MH is equal to the optical path from it to the auto-focus detector AF.

To overcome mechanical production tolerances, the minimum distance DH is factory preset so that once the AF system has been activated, the in focus spot diameter of the working $CO_2$ beam will be minimum. Thus, when changing working distance, the surgeon simply activates the AF device and the system will be refocused in the same manner as described in the lens-based system of FIGS. 1-4.

Figure 6:
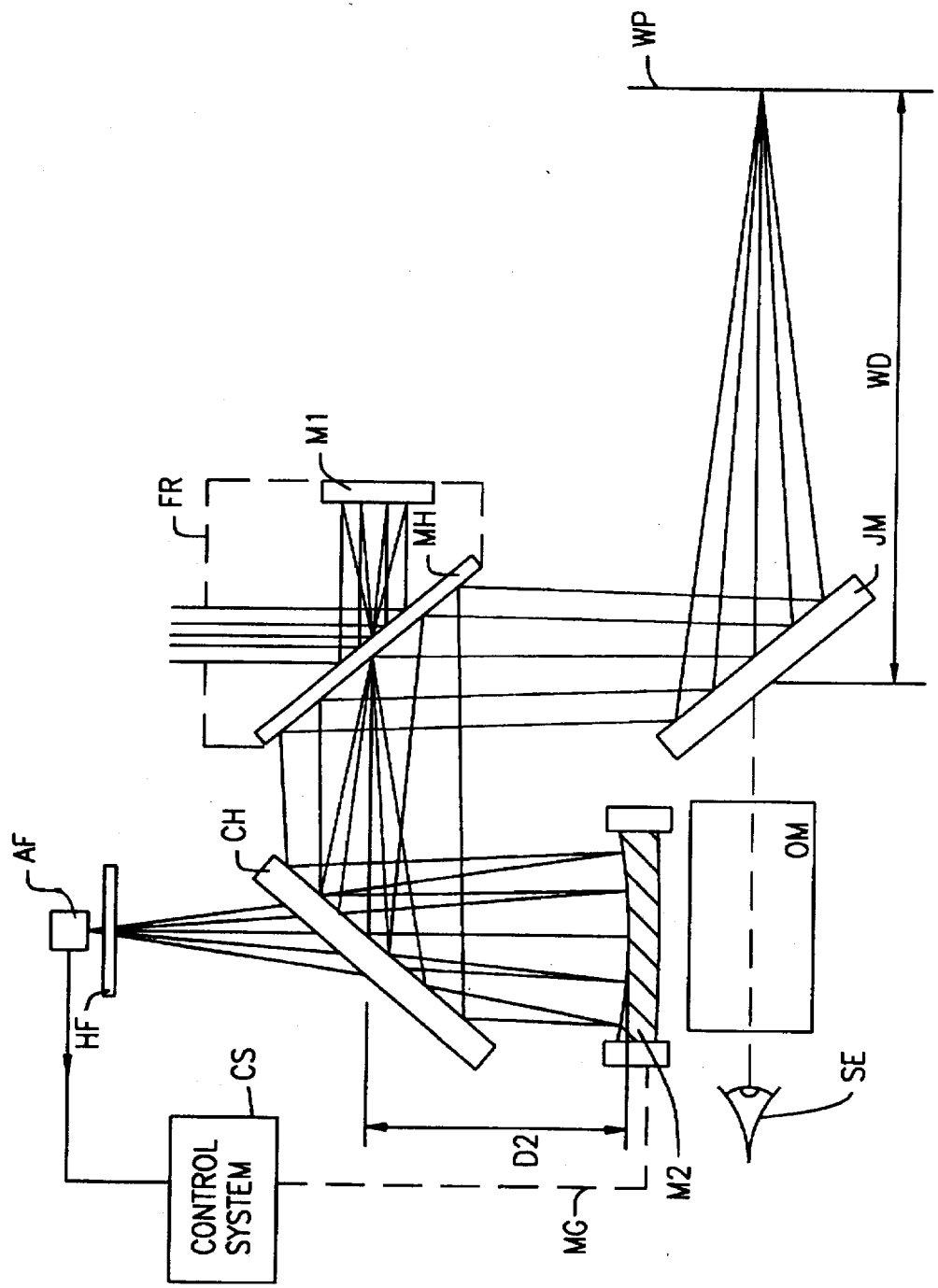

For example, in FIG. 6 the working distance is one-half of that represented by FIG. 5. Here, the AF device has focused the system by increasing the distance D2 activated by the motor and gear mechanism through the auto-focus control system (CS, FIG. 1).

Figure 7:
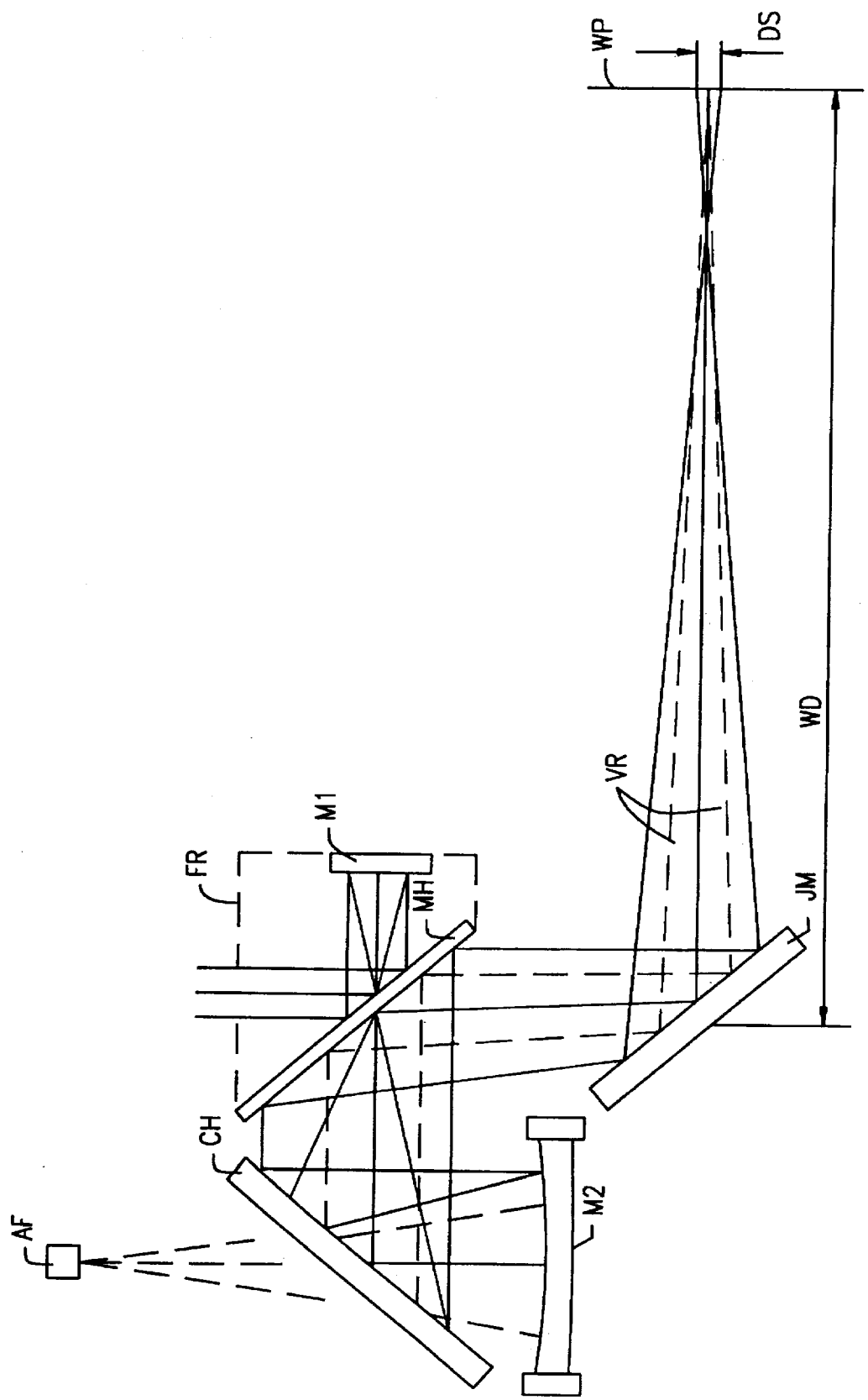
Figure 8:
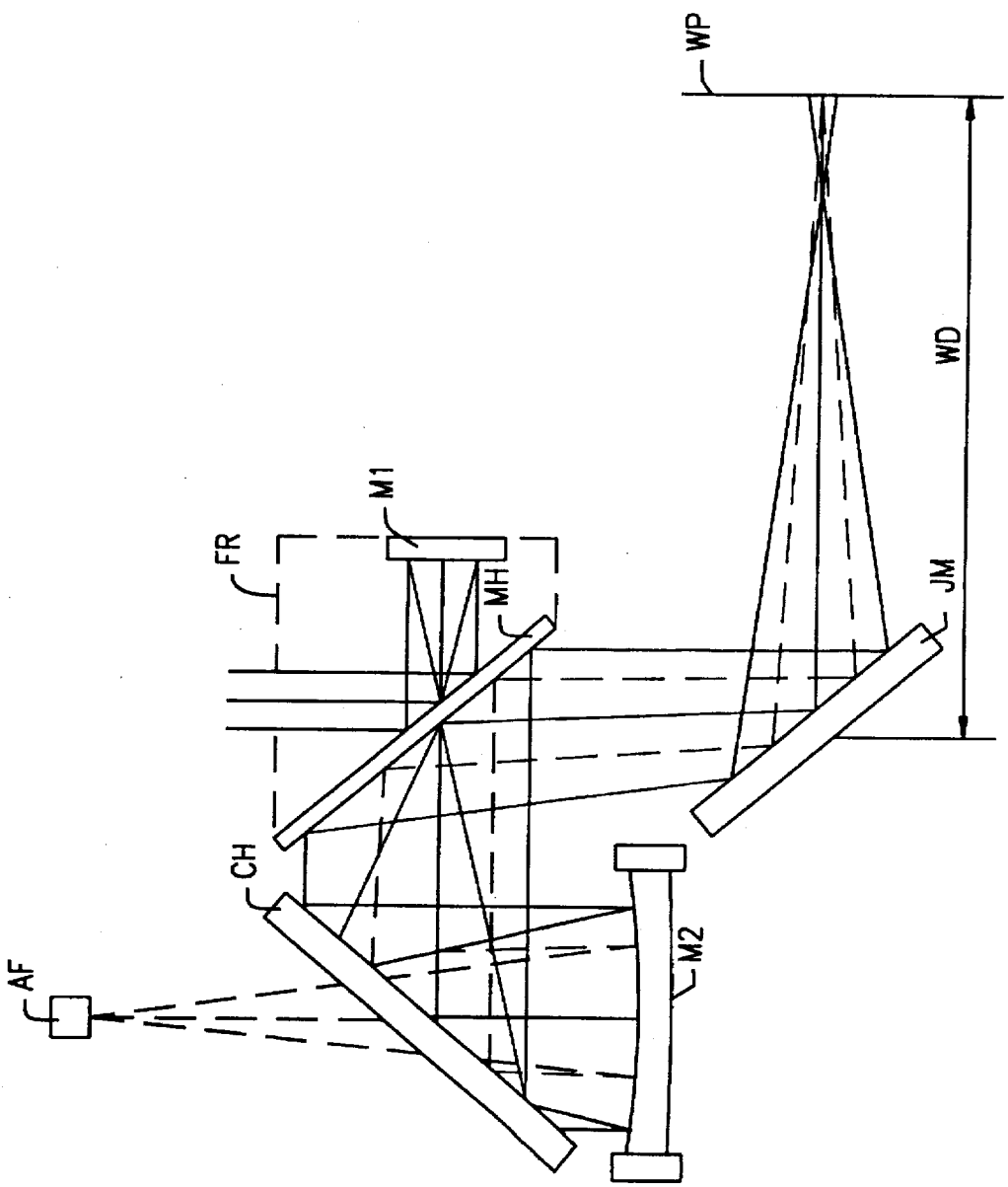

If the surgeon decides to work in an enlarged spot-diameter ("defocus") mode, the surgeon simply increases the distance DH of the first concave mirror M1 from reflector MH, e.g., by rotating a focusing ring FR as described in FIGS. 1-4. In this way as shown in FIGS. 7 and 8, the surgeon can operate in a coarsely focused ("defocus") or sharply focused mode without affecting the ray path of the AF device in the same manner as described in the lens-based system of FIGS. 1-4.

While the invention has been described with respect to two preferred embodiments, it will be appreciated that these are set forth merely for purposes of example, and that many other variations, modifications and applications of the invention may be made.

What is claimed is:

1. A mirror-based laser micromanipulator comprising:
   a laser source outputting both a $CO_2$ treatment laser beam and a HeNe visible aiming laser beam;

a planar reflector having first and second silvered sides, with a conical hole drilled in the center of said planar reflector;

said planar reflector positioned to receive the treatment and aiming beams, and reflect said beams from said first silvered side to reach a concave hyperbolic focussing mirror;

said concave hyperbolic focusing mirror receiving, reflecting, and focusing the treatment and aiming beams such that said beams pass through said conical hole in said planar reflector to reach a concave spherical focusing mirror;

said concave spherical focusing mirror reflecting said treatment and aiming beams to reach said second silvered side of said planar reflector;

said planar reflector receiving said treatment and aiming beams, and reflecting said treatment and aiming beams from said second silvered side to reach a manipulable mirror, said manipulable mirror receiving said treatment and aiming beams, and reflecting said laser beams to reach a working plane.

* * * * *